United States Patent
Sano (10) Patent No.: US 9,470,623 B2
(45) Date of Patent: Oct. 18, 2016

(54) PROPERTY MEASUREMENT SYSTEM FOR METAL MATERIAL

(75) Inventor: Mitsuhiko Sano, Minato-ku (JP)

(73) Assignee: TOSHIBA MITSUBISHI-ELECTRIC INDUSTRIAL SYSTEMS CORPORATION, Tokyo (JP)

( * ) Notice: Subject to any disclaimer, the term of this patent is extended or adjusted under 35 U.S.C. 154(b) by 0 days.

(21) Appl. No.: 14/001,893

(22) PCT Filed: Feb. 28, 2011

(86) PCT No.: PCT/JP2011/054481
§ 371 (c)(1),
(2), (4) Date: Aug. 28, 2013

(87) PCT Pub. No.: WO2012/117493
PCT Pub. Date: Sep. 7, 2012

(65) Prior Publication Data
US 2013/0335745 A1    Dec. 19, 2013

(51) Int. Cl.
G01B 11/02 (2006.01)
G01N 21/17 (2006.01)
G01N 29/24 (2006.01)
G01N 29/46 (2006.01)

(52) U.S. Cl.
CPC ...... *G01N 21/1702* (2013.01); *G01N 29/2418* (2013.01); *G01N 29/46* (2013.01); *G01N 2291/0234* (2013.01)

(58) Field of Classification Search
CPC ............. G01N 29/2418; G01N 29/46; G01N 21/1702; G01N 2291/0234; G01H 9/00; G01B 11/0666; G01B 11/161; G01D 5/266
See application file for complete search history.

(56) References Cited

U.S. PATENT DOCUMENTS 5,402,233 A * 3/1995 Schultz et al. ............... 356/493
5,585,921 A * 12/1996 Pepper ................ G01N 29/075
356/432
5,748,317 A * 5/1998 Maris et al. .................. 356/502

(Continued)

FOREIGN PATENT DOCUMENTS

JP    2001-272226 A    10/2001
JP    2001 318081       11/2001

(Continued)

OTHER PUBLICATIONS

Machine Translation of Ochiai et al. JP 2008116209 A.*

(Continued)

*Primary Examiner* — Michael A Lyons
(74) *Attorney, Agent, or Firm* — Oblon, McClelland, Maier & Neustadt, L.L.P.

(57) ABSTRACT

A property measurement system for a metal material includes: a laser oscillator that emits a pulse laser beam; a lens array that has small lenses with a same shape, the small lenses being laid in a matrix on a plane perpendicular to an optical axis of the pulse laser beam, and arranged so that a part of a cross section of the pulse laser beam can be made incident onto each of small lenses; a condensing lens that overlaps and condenses emitted beams coming from the small lenses on a same region of a surface of a metal material as a measurement target; a laser interferometer that detects, as an electric signal, a pulse ultrasonic wave that is excited by the pulse laser beam condensed and propagates through an inside of the metal material; and a signal processing device that processes the electric signal.

4 Claims, 8 Drawing Sheets

(56) References Cited

U.S. PATENT DOCUMENTS

| | | | |
|---|---|---|---|
| 6,253,621 B1* | 7/2001 | Jarvis | 73/655 |
| 6,666,094 B1* | 12/2003 | Sauerland | G01B 17/02 73/599 |
| 7,262,861 B1* | 8/2007 | Pepper | G01B 11/06 356/502 |
| 2001/0028460 A1 | 10/2001 | Maris et al. | |
| 2005/0200961 A1* | 9/2005 | Rosenbluh et al. | 359/626 |
| 2006/0215174 A1* | 9/2006 | Dubois | G01H 9/00 356/502 |
| 2008/0007717 A1* | 1/2008 | Nielsen | G01N 29/2418 356/73 |
| 2009/0090187 A1* | 4/2009 | Sano | G01N 29/2418 73/655 |

FOREIGN PATENT DOCUMENTS

| | | | |
|---|---|---|---|
| JP | 2002 257793 | | 9/2002 |
| JP | 2008 116209 | | 5/2008 |
| JP | 2008116209 A | * | 5/2008 |
| JP | 2009 115830 | | 5/2009 |
| KR | 10-2005-0046083 A | | 5/2005 |

OTHER PUBLICATIONS

International Search Report Issued Mar. 29, 2011 in PCT/JP11/054481 filed Feb. 28, 2011.
Office Action issued Aug. 26, 2015 in Korean Patent Application No. 10-2015-7017076 (with English language translation).

* cited by examiner

PROPERTY MEASUREMENT SYSTEM FOR METAL MATERIAL

TECHNICAL FIELD

The present invention relates to a property measurement system for metal materials, which uses a laser beam.

BACKGROUND ART

In recent years, enhancement of metal material properties such as strength and formability has been remarkable. Following this, there has risen a necessity to measure such properties of metal materials and a variety of other properties, which have strong correlations with the aforementioned properties of the metal materials, in the manufacturing process and inspection process.

For example, there is a strong correlation between the strength and the grain size of such a metal material, and it is known that, if the grain size is reduced to an approximate range from several 10 µm to 1 µm, a high-performance metal material which not only has high strength but also excellent processability and recyclability, is obtained. It is frequent that quality control of the metal material, which is as described above, is performed by a destructive test. For example, a test piece is cut out from a product coil already subjected to a rolling process, and strength thereof is confirmed by a tensile test. However, in such a method, the lead time until a measurement value is obtained is as long as several hours to several days, and defective products cannot be prevented from occurring continuously during this time.

To solve this problem, property measurement of the metal material by a laser ultrasonic wave method is attempted (for example, refer to PTL 1). The laser ultrasonic wave method is a method for measuring the metal material properties such as the grain size in a non-contact manner by irradiating a pulse laser beam onto a surface of the metal material and analyzing the propagation behavior of a pulse-like ultrasonic wave (hereinafter, referred to as a "pulse ultrasonic wave") in the metal material, the ultrasonic wave having a high frequency generated at the time when the pulse laser beam is irradiated. In accordance with this method, measurement results are obtained rapidly.

The properties of the metal material, which are to be detected by using the propagation behavior of the pulse ultrasonic wave, are various, for example; the grain size, the elasticity, the formability (r-value), the elastic wave velocity and the like. Moreover, it is known that there are strong correlation relationships between the grain size of the metal material and tensile strength, yield strength and yield elongation, and thus values for these properties can also be obtained by a similar measurement method to that used to measure the grain size of the metal material.

CITATION LIST

Patent Literature

[PTL 1] Japanese Patent Laid-Open Publication No. 2008-116209

SUMMARY OF INVENTION

Technical Problem

When measuring the properties of the metal material using the laser ultrasonic wave method, during the period while the pulse ultrasonic wave is propagating through the inside of the metal material, amplitude of the pulse ultrasonic wave is reduced not only by "(i) attenuation of the pulse ultrasonic wave by scattering thereof on a grain boundary", which is used for the property measurement for the metal material, but also by "(ii) diffusion of the pulse ultrasonic wave in directions other than a straight-ahead direction". When the amplitude of the pulse ultrasonic wave is reduced, the signal-to-noise ratio is deteriorated, and measurement accuracy of the property measurement system is lowered.

Hence, in order to more clearly detect the attenuation of the pulse ultrasonic wave by the scattering thereof on the grain boundary, it is necessary to suppress the diffusion of the pulse ultrasonic wave. In order to suppress the diffusion of the pulse ultrasonic wave, there is a method of increasing the spot size of the pulse laser beam. That is to say, on an outer circumferential portion of the spot, oscillations are restrained by the metal material on the periphery thereof, and accordingly, the traveling direction of the pulse ultrasonic wave is changed, and the diffusion occurs; however, if the spot size is increased, then the influence of the outer circumferential portion can be relatively reduced, and the diffusion of the pulse ultrasonic wave in directions other than the straight-ahead direction can be suppressed.

However, there has been a problem that a sufficient effect cannot be obtained only by simply amplifying and irradiating a pulse laser beam to be emitted from a general laser oscillator. That is to say, in general, the light quantity distribution (beam profile) in the beam cross section of the pulse laser beam to be emitted from the laser oscillator is not uniform, and the light quantity in the vicinity of the center of the beam is larger than that on the periphery thereof. Therefore, in the case where the pulse laser beam is simply amplified to thereby increase the spot size, amplitude of the pulse ultrasonic wave to be excited on the center portion of the spot in the metal material is large, and amplitude of the pulse ultrasonic wave to be excited on the peripheral portion of the spot therein is small.

Owing to such an amplitude difference between the pulse ultrasonic waves, the propagation direction of the pulse ultrasonic wave is not aligned with the direction perpendicular to the irradiation surface of the pulse laser beam, and the pulse ultrasonic wave is diffused to the periphery as in the case where the spot size is small. Therefore, the amplitude of the pulse ultrasonic wave is remarkably reduced with respect to the propagation distance, and the signal-to-noise ratio of the waveform of the pulse ultrasonic wave to be detected is deteriorated. As a result, there has been a problem that the measurement accuracy is lowered.

In consideration of the above-described problems, it is an object of the present invention to provide a property measurement system for a metal material, which uses a pulse laser beam, in which the lowering of the measurement accuracy is suppressed.

Solution to Problem

In accordance with an aspect of the present invention, there is provided a property measurement system for a metal material, including: (A) a laser oscillator that emits a pulse laser beam; (B) a lens array that has a plurality of small lenses with the same shape, the small lenses being laid in a matrix on a plane perpendicular to the optical axis of the pulse laser beam, and arranged so that a part of the cross section of the pulse laser beam can be made incident onto each of the plurality of small lenses; (C) a condensing lens that overlaps and condenses emitted beams coming from the plurality of small lenses of the lens array on the same region of a surface of a metal material as a measurement target; (D) a laser interferometer that detects, as an electric signal, a pulse ultrasonic wave that is excited by the pulse laser beam condensed by the condensing lens and propagates through the inside of the metal material; and (E) a signal processing device that processes the electric signal.

Advantageous Effects of Invention

In accordance with the present invention, there can be provided the property measurement system for a metal material, which uses a pulse laser beam, in which the lowering of the measurement accuracy is suppressed.

BRIEF DESCRIPTION OF DRAWINGS

FIG. 2 is schematic views showing a configuration example of a lens array owned by the property measurement system for a metal material according to the first embodiment of the present invention.

FIG. 6 is a graph showing an example of a light quantity distribution of a pulse laser beam.

FIG. 11 is photographs showing a chronological change of a beam profile of the pulse laser beam.

DESCRIPTION OF EMBODIMENTS

Next, a description is made of first and second embodiments of the present invention with reference to the drawings. In the following description referring to the drawings, the same or similar reference numerals are assigned to the same or similar portions. The first and second embodiments to be shown below are one illustration of an apparatus and a method for embodying a technical idea of this invention, but the embodiments of this invention are not limited to the specific structures, arrangements and the like of constituent components to be described below. The embodiments of this invention can be changed in various ways within the scope of the claims.

First Embodiment

Figure 1:
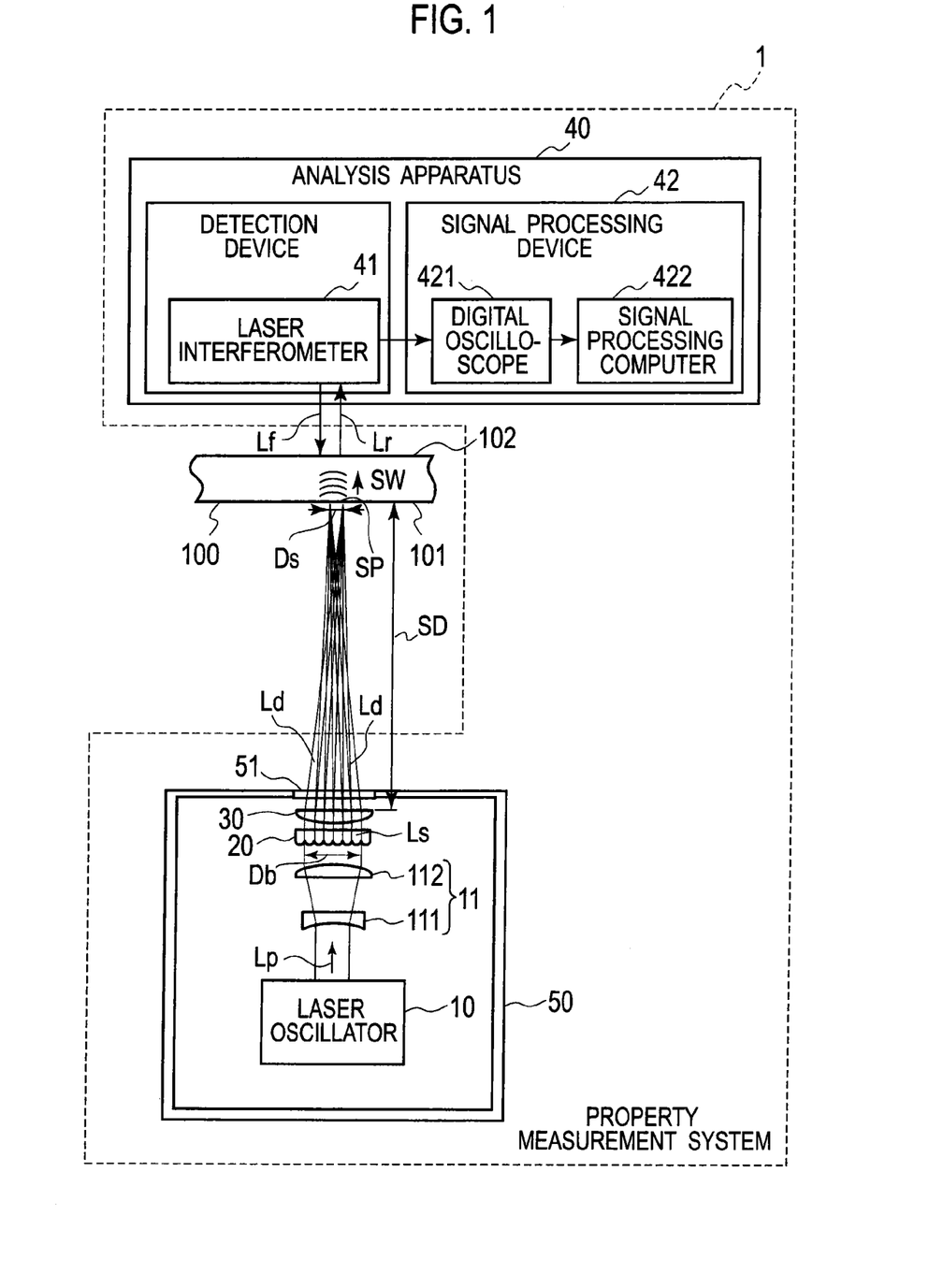
FIG. 1 is a schematic view showing a configuration of a property measurement system for a metal material according to a first embodiment of the present invention.

As shown in FIG. 1, a property measurement system 1 for a metal material according to a first embodiment of the present invention includes: a laser oscillator 10 that emits a pulse laser beam Lp; a lens array 20 having a plurality of small lenses Ls with the same shape, which are laid in a matrix on a plane perpendicular to the optical axis of the pulse laser beam Lp; a condensing lens 30 that overlaps and condenses emitted beams Ld, which are emitted from the plurality of small lenses Ls, on the same region of a surface 101 of a metal material 100 as a measurement target; and an analysis apparatus 40 that analyzes a pulse ultrasonic wave SW that propagates the inside of the metal material 100 as a result of the emitted beams Ld irradiated onto the surface 101. Onto the plurality of small lenses Ls, a part of the cross section of the pulse laser beam Lp, perpendicular to the optical axis thereof, is individually made incident, and the plurality of small lenses Ls individually emit the emitted beams Ld in which shapes of beam cross sections perpendicular to the optical axis are mutually the same.

In the property measurement system 1 shown in FIG. 1, the pulse laser beam Lp is irradiated onto the surface 101 of the metal material 100, whereby small-scale explosions are caused there, and the pulse ultrasonic wave SW is excited in the metal material 100. This pulse ultrasonic wave SW is attenuated while propagating through the inside of the metal material 100, and appears as minute oscillations on a back surface 102 of the metal material 100, which is opposite to the surface 101 onto which the pulse laser beam Lp is irradiated.

A detection device of the analysis apparatus 40 detects the minute oscillations as an electric signal. FIG. 1 shows an example of employing a laser interferometer 41 as the detection device. The laser interferometer 41 detects, as the electric signal, the pulse ultrasonic wave that is excited by the process of the pulse laser beam Lp being condensed by the condensing lens 30 and propagating through the inside of the metal material 100. Specifically, the laser interferometer 41 irradiates a weak detection laser beam Lf onto the back surface 102 of the metal material 100. This creates a reference illuminant and reflected light Lr of the detection laser beam Lf, which come from the metal material 100 and interfere with each other. The minute oscillations which have appeared on the back surface 102 of the metal material 100 are thereby detected as a change of voltage. A signal processing device 42 of the analysis apparatus 40 processes the electric signal detected by the laser interferometer 41, whereby properties of the metal material 100 are measured. For example, the detected electric signal is captured to a signal processing computer 422 through a digital oscilloscope 421, and the properties of the metal material 100 are determined by waveform analysis.

A description is made below of details of the property measurement system 1 shown in FIG. 1.

For the laser oscillator 10, for example, it is possible to employ a Q-switch solid pulse laser with a large and stable output. In particular, a Q-switch solid pulse laser with a pulse width approximately ranging from several nanoseconds to several tens of nanoseconds, and which uses neodymium-doped: yttrium aluminum garnet (Nd:YAG) for an oscillation solid medium, as is widely used for industrial purposes, is suitable for the laser oscillator 10.

In general, the pulse laser beam Lp to be emitted from the laser oscillator 10 has a slight divergence angle. Therefore, the pulse laser beam Lp is turned to substantially parallel light by using a magnification system 11 in which a concave lens 111 and a convex lens 112 are combined with each other, such that the beam is incident onto the lens array 20.

Figures 2A, 2B:
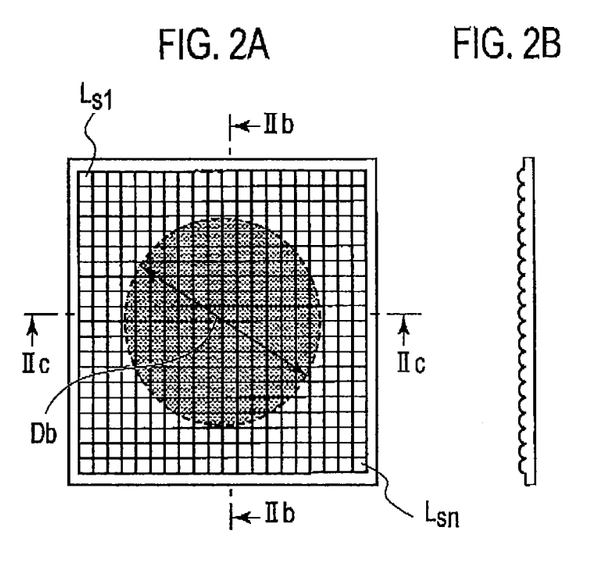
FIG. 2(a) is a plan view.
FIG. 2(b) is across-sectional view along a IIb-IIb direction of FIG. 2(a)
Figure 2C:
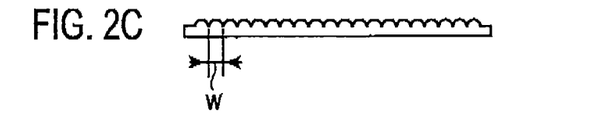
FIG. 2(c) is a cross-sectional view along a IIc-IIc direction of FIG. 2(a).

FIGS. 2(a) to 2(c) show a configuration example of the lens array 20. The lens array 20 has a structure in which a large number of the small lenses Ls with the same shape are laid on the plane perpendicular to the optical axis of the pulse laser beam Lp to be made incident thereonto. FIG. 2 shows an example where n small square lenses Ls1 to Lsn are arranged in the matrix. The region which is hatched in FIG. 2(a), is a region to be irradiated with the pulse laser beam Lp, and the beam diameter of the pulse laser beam Lp is Db.

Besides a square, it is possible to employ any shape such as a rectangle, a hexagon and a circle for the small lenses Ls. Note that, if there are gaps among the small lenses Ls, then condensation efficiency is lowered, and accordingly, it is preferable that the small lenses Ls be arranged without gaps interposed thereamong in the lens array 20. A lens pitch w of the small lenses Ls, which is shown in FIG. 2(c), is determined so that, as will be described later, a sufficient number of the small lenses Ls can be included in the beam cross section of the pulse laser beam Lp to be made incident thereonto. Here, the "lens pitch of the small lenses Ls" is the distance between centers of the small lenses Ls adjacent to each other.

When the pulse laser beam Lp is made incident onto the lens array 20, a part of the cross section of the pulse laser beam Lp is made incident onto each of the small lenses Ls which compose the lens array 20. The small lenses Ls are arranged so as to intercept a part of the beam cross section of the pulse laser beam Lp concerned, such that each of the small lenses Ls forms an image of the shape (for example, a square) of the small lenses Ls. Whatever the distribution of light quantity (beam profile) of the beam cross section of the pulse laser beam Lp to be made incident onto the lens array 20 may be, the emitted beams Ld of the respective small lenses Ls, which are created from an extremely small proportion of the pulse laser beam Lp, have a uniform light distribution.

The respective emitted beams Ld emitted from the lens array 20 are condensed on the surface 101 of the metal material 100 by the condensing lens 30 that is a convex lens. Note that the focal length of the condensing lens 30 is substantially equal to the standoff distance SD (interval between the condensing lens 30 and the surface 101 of the metal material 100).

Then, the respective images from the plurality of small lenses Ls are superimposed and projected on the focal position of the condensing lens 30, that is, one point on the surface 101 of the metal material 100. In order to achieve this, the pulse laser beam Lp may need to be reconfigured so that a condensed spot SP, which is to be irradiated with the plurality of pulse laser beams with the uniform light quantity distribution and the same shape (for example, a square) as that of the small lenses Ls, can be formed on the surface 101 of the metal material 100. The shape of the condensed spot SP is the same as the shape of the small lenses Ls, and the size thereof is determined by the focal length of the condensing lens 30.

In the condensed spot SP, the images projected by the plurality of small lenses Ls are superimposed on one another, and accordingly, brightness irregularities due to interference fringes occur. However, if the number of images to be superimposed on one another is increased sufficiently, the interval between the interference fringes can be reduced to a negligible size, and a substantially uniform light quantity distribution can be obtained on the condensed spot SP. When the number of images to be superimposed on one another falls below 15, then in some cases, the influence of the interference fringes, of the waveform of the pulse ultrasonic wave SW that propagates through the inside of the metal material 100, cannot be ignored, and in addition, the ability to uniform the light quantity becomes insufficient. Hence, the lens pitch of the small lenses Ls in the lens array 20 is set so that 15 or more small lenses Ls can be included in the beam cross section of the pulse laser beam Lp to be made incident.

The focal length of the lens array 20 is decided by an experiment or a ray trace simulation calculation so that the size of the condensed spot SP to be formed on the surface 101 of the metal material 100 can have a desired value. Practically, the focal length of the lens array 20 is within an approximate range from a value equivalent to the standoff distance SD to one-tenth of the standoff distance SD. Since there are a variety of restrictions in manufacturing the lens array 20, such small lenses Ls with the desired focal length cannot be obtained in some cases. In this case, a plurality of the lens arrays 20 may be arranged in combination with one another.

In the pulse laser beam Lp, the peak value of light density is high. Accordingly, a glass-made material such as quartz glass, for example, in which the damage threshold value is high, is suitable as a raw material of the lens array 20. However, a plastic-made lens array 20 or the like is also employable depending on the wavelength and the output necessary for the property measurement of the metal material 100.

Figure 3:
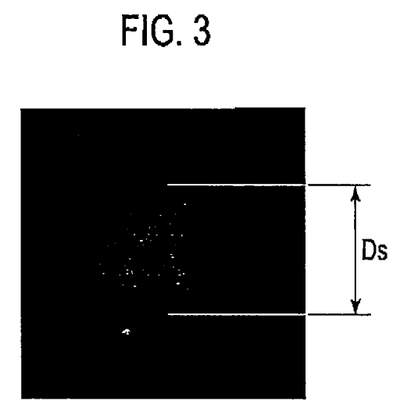
FIG. 3 is a photograph showing an example of a shape of a condensed spot generated by the property measurement system for a metal material according to the first embodiment of the present invention.

FIG. 3 shows an example where the shape of the condensed spot SP on the surface 101 of the metal material 100 is printed and recorded on burn paper. FIG. 3 shows the shape of the condensed spot SP formed by allowing the pulse laser beam Lp with the beam diameter Db of 14 mm, to be incident onto the lens array 20 in which the small lenses Ls are arranged with a pitch of 1.1 mm in a matrix with 18 rows and 18 columns. Hence, FIG. 3 shows an example where images of approximately 127 small lenses Ls are superimposed on one another. The shape of the condensed spot SP is square which is the same as the shape of the small lenses Ls of the lens array 20, and it is understood that the shapes of the small lenses Ls are projected while being superimposed on one another in a good manner. In the example shown in FIG. 3, the size Ds of the condensed spot Sp is 4.5 mm.

Figure 4:
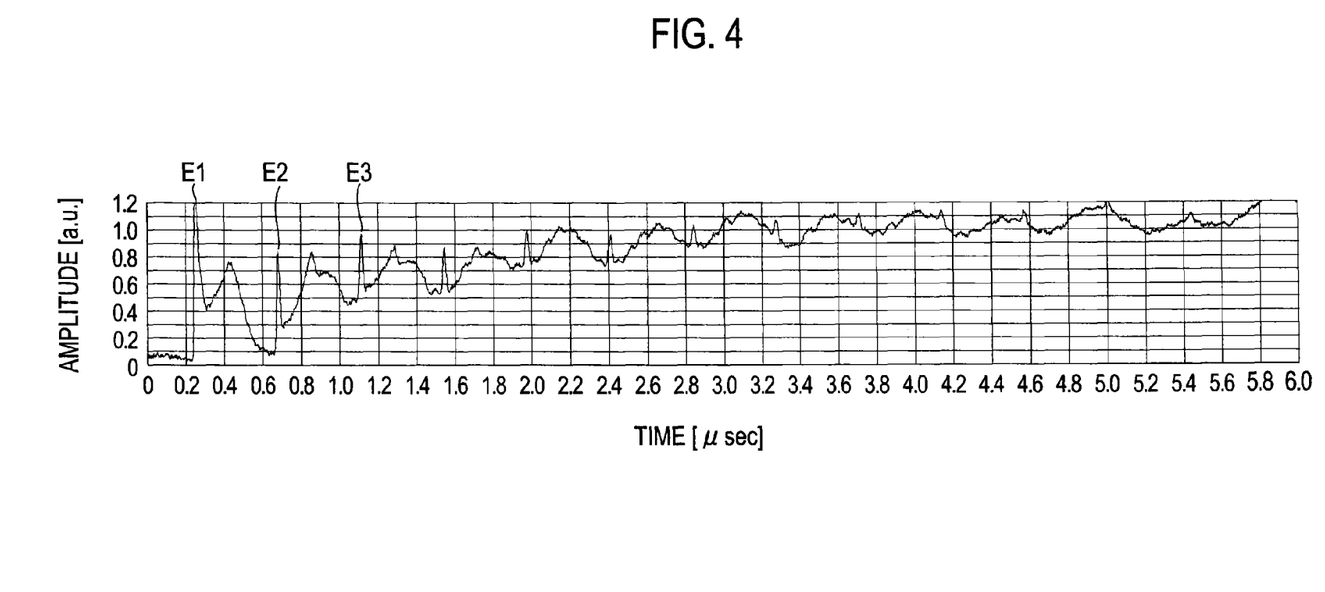
FIG. 4 is a graph showing an example of a detection waveform of a pulse ultrasonic wave to be excited in an inside of a metal material as a measurement target.

By the irradiation of the pulse laser beam Lp onto the condensed spot Sp, the pulse ultrasonic wave SW is excited in the metal material 100, and this pulse ultrasonic wave SW propagates through the inside of the metal material 100. As illustrated in FIG. 4, the pulse ultrasonic wave SW to be excited in the metal material 100 has components of a variety of oscillation modes. For example, for measurement of the grain size of the metal material 100, multiple reflection echoes (pointed portions of the waveform, which are shown by arrows in FIG. 4) of longitudinal wave components are utilized. In FIG. 4, waveforms E1, E2, and E3 are a first echo, second echo and third echo of the longitudinal wave, respectively.

Note that, in FIG. 4, the axis of ordinates represents relative amplitude (unit: a.u. (Arbitrary Unit)) and the axis of abscissas is elapsed time from the emission of the pulse laser beam Lp. The first echo is detected at the point of time when the pulse ultrasonic wave SW reaches the back surface 102 of the metal material 100 for the first time after the pulse laser beam Lp is emitted. Subsequent echoes are detected each time the pulse ultrasonic wave SW returns to the back surface 102 after having reflected off the back surface 102 and surface 101. Hence, the time until the first echo is detected corresponds to the thickness of the metal material 100, and intervals between which the respective subsequent echoes are detected correspond to multiples of double the thickness of the metal material 100.

Figure 5:
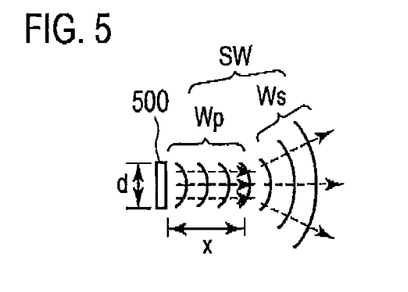
FIG. 5 is a schematic view showing a state where a pulse ultrasonic wave transmitted from a piston sound source is diffused.

Here, with reference to FIG. 5, a description is made of the pulse ultrasonic wave SW that propagates through the inside of the metal material 100. FIG. 5 is a schematic view showing a state where the pulse ultrasonic wave SW transmitted from a planar piston sound source 500 is diffused.

In the case where the pulse ultrasonic wave SW is transmitted from the piston sound source 500, the region where the pulse ultrasonic wave SW goes straight as a plane wave Wp is referred to as the near field (Fresnel zone), and the distance (near field limit distance x) over which the pulse ultrasonic wave SW goes straight is represented by the following Expression (1):

$$x = d^2/(4\lambda) \quad (1)$$

In Expression (1), d is the diameter of the piston sound source 500, which is equivalent to the spot size of the pulse laser beam Lp irradiated onto the metal material 100. $\lambda$ is the wavelength (mm) of the pulse ultrasonic wave SW.

Meanwhile, the region beyond the near field limit distance x is referred to as the far field, and here the pulse ultrasonic wave SW is diffused as a spherical wave. In the far field, irrespective of the material properties such as the grain size, the amplitude of the pulse ultrasonic wave SW is rapidly decreased in proportion to the square of the propagation distance. Hence, in order to clearly detect the pulse ultrasonic wave SW for use in the waveform analysis, it is preferable to increase the spot size and to further lengthen the near field limit distance x.

For example, in the event of measuring the grain size of a steel material with a thickness of 2 mm, in the case of detecting the waveforms of the first to fifth echoes in the multiple reflections from the back surface of the steel material, the propagation distance of the fifth echo is represented by the following Expression (2):

$$2 \text{ (mm)} \times (1 + 4 \times 2 (\text{laps})) = 18 \text{ (mm)} \quad (2)$$

The propagation velocity v of a longitudinal ultrasonic wave of the steel material is approximately 5900 m/s, and accordingly, the wavelength $\lambda = v/f$ of a longitudinal ultrasonic wave of 30 MHz is 0.197 mm. Hence, in accordance with Expression (1), it is understood that, in the case of using a frequency component of 30 MHz or more for the waveform analysis, preferably, the diameter of the spot size is set at approximately 4 mm or more.

Numeric values described above are related to design, and actually, there is also a case where no problem occurs even if a smaller spot size is adopted depending on to what extent the deterioration of the signal-to-noise ratio can be permitted given the measurement purpose. Moreover, there is also a case where, even in the case where the spot size is smaller, the ultrasonic wave echoes can be clearly detected in such a manner that the ultrasonic waveform is corrected by using a publicly known expression that represents a decrease of the amplitude by the diffusion, and the like.

Meanwhile, with regard to suppression of the diffusion of the pulse ultrasonic wave SW, restrictions on an upper limit of the spot size are not particularly strict. However, in response to the output of the laser oscillator 10, there is an upper limit value of the spot size, at which the light quantity density can ensure ablation on the surface 101 of the metal material 100. Accordingly, the spot size just needs to be equal to or less than the upper limit value concerned. Hence, it is not particularly necessary to adjust the upper limit of the spot size in response to the thickness and the like of the metal material 100.

Figure 6A:
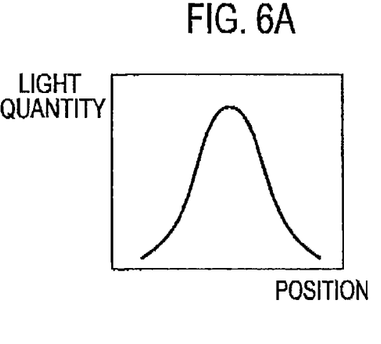
FIG. 6(a) shows a Gaussian distribution.
Figure 6B:
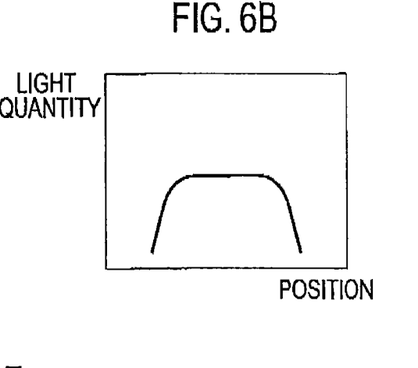
FIG. 6(b) shows a uniform distribution.

The above-described study for the diffusion of the pulse ultrasonic wave SW is premised on the planar piston sound source 500. However, the light quantity distribution (beam profile) in the beam cross section of the pulse laser beam Lp to be emitted from the laser oscillator 10 is not necessarily uniform. In particular, the light quantity distribution of the pulse laser beam of the laser oscillator widely used for industrial purposes is a Gaussian distribution (normal distribution), in which the light quantity in the vicinity of the beam center is large and hence the laser condensability is good. Any distribution approximate to this is also suitable. In the case where the beam profile is of the Gaussian distribution as shown in FIG. 6(a), the difference between the light quantity in the vicinity of the beam center and the light quantity on the periphery thereof is larger in comparison with the case shown in FIG. 6(b), where the beam profile is uniform. Note that axes of ordinates of FIG. 6(a) and FIG. 6(b) represent the light quantity, and that axes of abscissas represent positions in the condensed spot.

In the case where the pulse laser beam having the Gaussian distribution is condensed with the sufficiently large spot size on the surface 101 of the metal material 100 as mentioned above, it is general that such condensation is carried out through an optical reduction system made of several lenses. In this case, as the light quantity distribution in the condensed spot is controlled by lenses, the light quantity distribution of the pulse laser beam to be emitted from the laser oscillator can be projected as it is. Therefore, in the center portion of the condensed spot, the amplitude of each ultrasonic wave echo to be excited is large, and on the contrary, in the peripheral portion of the condensed spot, the amplitude of each ultrasonic wave echo to be excited is small. As already mentioned, owing to this amplitude difference, the pulse ultrasonic wave is diffused to the periphery as in the case where the spot size is small. As a result, the signal-to-noise ratio of the waveform of the ultrasonic wave, which is to be detected by the laser interferometer, is deteriorated, and measurement accuracy is lowered.

However, in accordance with the property measurement system 1 shown in FIG. 1, the plurality of small lenses Ls which compose the lens array 20 superimpose and project the images which have uniform light quantity distribution, on the focal position of the condensing lens 30. Therefore, the pulse laser beam Lp is reconfigured so that a condensed spot, which has the same shape as that of the small lenses Ls, and has a uniform light quantity distribution as shown in FIG. 6(b), can be formed on the surface 101 of the metal material 100.

Hence, the diffusion of the pulse ultrasonic wave SW to be excited in the metal material 100 by the pulse laser beam Lp can be suppressed to be small. As a result, the amplitude of the pulse ultrasonic wave SW is less likely to be reduced with respect to the propagation distance.

The pulse ultrasonic wave SW excited by the pulse laser beam Lp propagates through the inside of the metal material 100, and the minute oscillations which appear on the back surface 102 of the metal material 100 are detected as electric signals by the laser interferometer 41. The amplitude of the pulse ultrasonic wave SW is suppressed from being decreased as described above, and accordingly, the signal-to-noise ratio of the waveform of the ultrasonic wave, which is to be detected by the laser interferometer 41, is enhanced, whereby it is possible to obtain good measurement accuracy.

For the laser interferometer 41, it is possible to employ a photorefractive interferometer capable of measuring high-frequency oscillations even if the surface 101 of the metal material 100 is a rough surface. Alternatively, in a similar way, it is also possible to employ a Fabry-Perot interferometer since the Fabry-Perot interferometer can measure the high-frequency oscillations on the rough surface. Moreover, it is also possible to employ a Michelson interferometer if the surface 101 of the metal material 100 is a mirror surface.

A voltage waveform detected by the laser interferometer 41 is recorded, for example, in the digital oscilloscope 421, and is analyzed by the signal processing computer 422, whereby the property measurement of the metal material 100 can be performed.

Due to attenuation of the longitudinal ultrasonic wave by the scattering thereof in the grains, the longitudinal ultrasonic wave propagating through the inside of the metal material 100, differs depending on the frequency of the longitudinal ultrasonic wave and the grain size of the metal material 100. For example, Rayleigh scattering, stochastic scattering and the like are known.

A description is made below of an example of a waveform analysis method, which is based on such scattering attenuation, with reference to the flowchart shown in FIG. 7.

Figure 7:
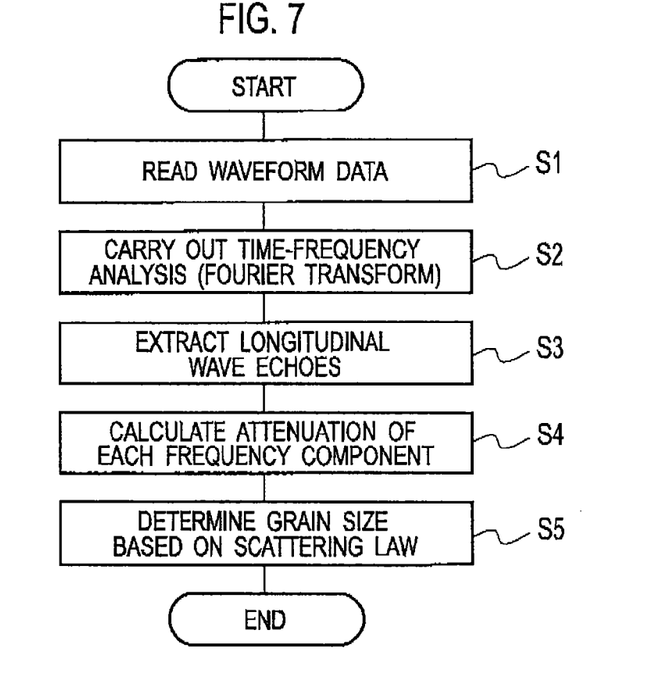
FIG. 7 is a flowchart for explaining an example of a waveform analysis method by the property measurement system for a metal material according to the first embodiment of the present invention.

Waveform data read in Step S1 of FIG. 7 is decomposed into the respective frequency components by a Fourier transform or the like in Step S2. Next, in Step S3, each of the longitudinal wave echoes is extracted in each of the respective frequency components. In Step S4, a change of amplitude of the extracted longitudinal wave echo is approximated by a logarithmic function, and an attenuation factor α(f) of each frequency component is calculated.

The attenuation factor α, the frequency f and the grain size D have a correlation relationship of the following Expression (3):

$$\alpha = K \times D^{n-1} \times f^n \quad (3)$$

In Expression (3), α is the attenuation factor (dB/mm), D is the grain size (mm), f is the frequency (MHz), and K and n are coefficients.

When Expression (3) is transformed, the following Expression (4) is obtained:

$$D = \{\alpha/(K \times f^n)\}^{1/(n-1)} \quad (4)$$

In Step S5, based on the attenuation factor α(f) of any frequency f, the grain size is determined based on Expression (4). Note that values of the coefficients K and n are predetermined by an experiment of measuring a test material in which the grain size is already known. Theoretically, the value of the coefficient n is determined in response to a ratio D/λ of the grain size D and the wavelength λ. That is to say, n is equal to 4 (n=4) in the Rayleigh scattering region (0.03≤D/λ≤0.3), and n is equal to 3 (n=3) in the stochastic scattering region (0.3≤D/λ≈1).

Figure 8:
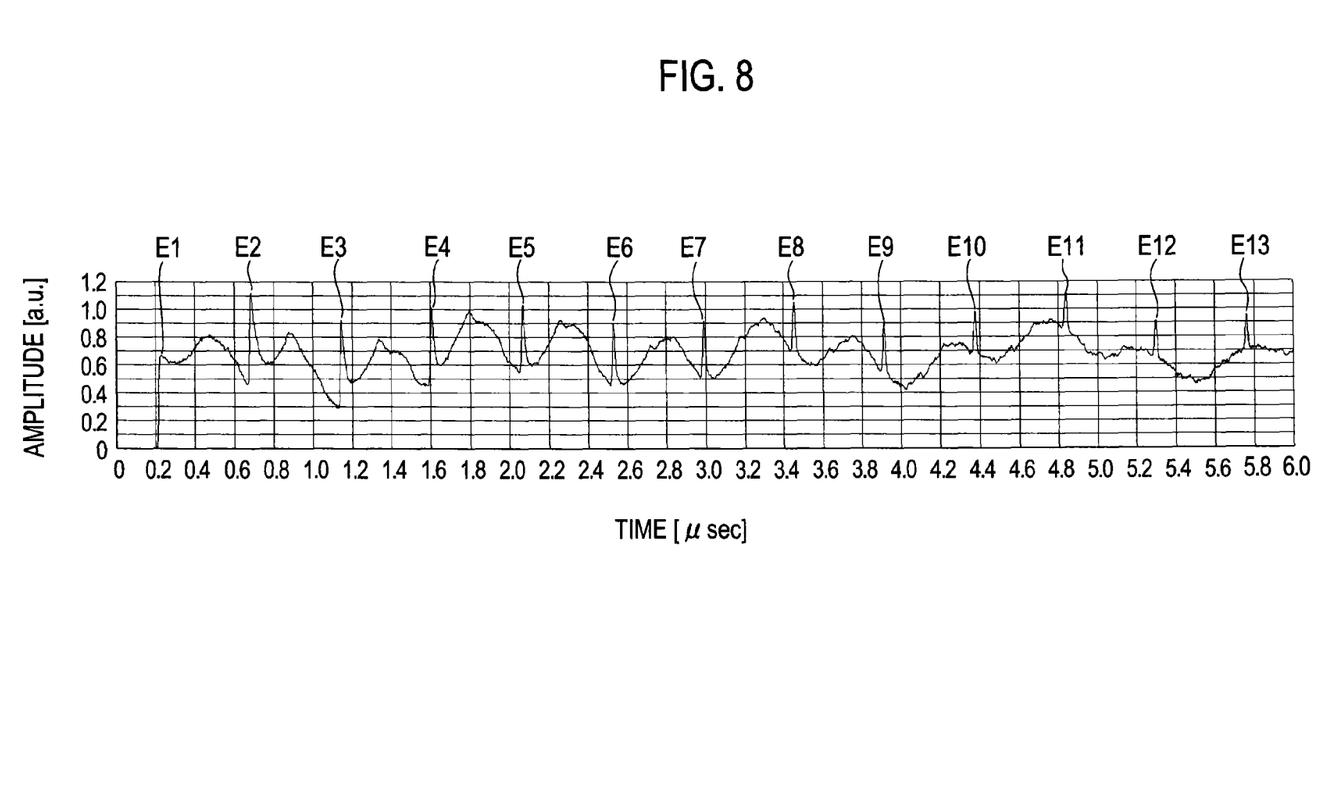
FIG. 8 is a graph showing an example of a detection waveform of the pulse ultrasonic wave detected by the property measurement system for a metal material according to the first embodiment of the present invention.

FIG. 8 is an example of the waveform of the ultrasonic wave, which is detected by the property measurement system 1 for a metal material according to the first embodiment. In FIG. 8, the axis of ordinates represents relative amplitude (unit: a.u. (Arbitrary Unit)). The axis of abscissas is the elapsed time from the emission of the pulse laser beam Lp. The metal material 100 as a measurement target is a steel plate with a plate thickness of 1.35 mm, and the grain size thereof is approximately 4 μm. Such an ultrasonic waveform detected by the laser interferometer 41 can be clearly detected from the first echo (waveform E1) of the longitudinal wave to the $13^{th}$ echo (waveform E13) thereof.

As described above, in accordance with the property measurement system 1 for a metal material according to the first embodiment of the present invention, the light quantity distribution in the beam cross section of the pulse laser beam to be irradiated onto the metal material 100 as the measurement target can be made uniform. Therefore, the diffusion of the pulse ultrasonic wave SW to be excited in the metal material 100 is suppressed. As a result, there is provided the property measurement system 1 for a metal material, which uses the pulse laser beam, in which the lowering of the measurement accuracy is suppressed.

Note that the positional relationship between the condensing lens 30 and the lens array 20 may be reversed back and forth from the example shown in FIG. 1. That is to say, the lens array 20 may be arranged between the laser oscillator 10 and the condensing lens 30, or alternatively, the condensing lens 30 may be arranged between the laser oscillator 10 and the lens array 20.

Figure 9:
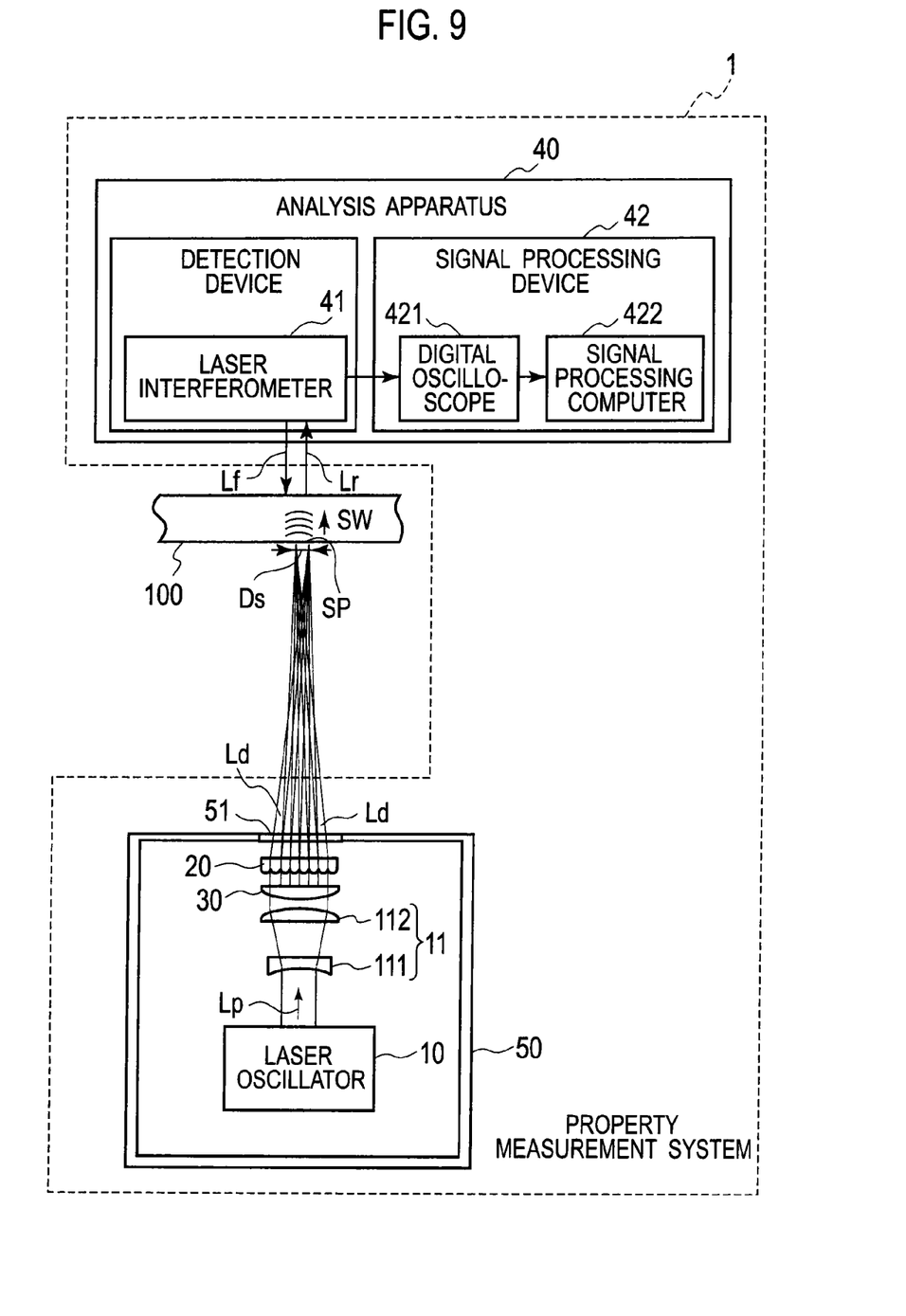
FIG. 9 is a schematic view showing another configuration of the property measurement system for a metal material according to the first embodiment of the present invention.

FIG. 9 shows an example where the condensing lens 30 is arranged between the laser oscillator 10 and the lens array 20. Also by a property measurement system 1 shown in FIG. 9, the emitted beams Ld to be individually outputted by the plurality of small lenses Ls of the lens array 20 can be condensed to the same region of the surface 101 of the metal material 100 as the measurement target by the condensing lens 30.

Moreover, as shown in FIG. 1 and FIG. 9, an aperture plate 51 is placed between the metal material 100 and the lens array 20 and the condensing lens 30. In order to emit the pulse laser beam Lp to the outside from a cabinet 50 in which the laser oscillator 10, the lens array 20 and the condensing lens 30 are housed, the aperture plate 51 is placed in the cabinet 50.

It is frequent that optical instruments such as lenses and reflecting mirrors, as well as the laser oscillator, are made of special raw materials or are subjected to special coating in order to enhance optical efficiency thereof. If dust and the like adhere to the optical instruments concerned, then the optical instruments are damaged with ease, and the optical efficiency thereof is lowered. Accordingly, in general, all of the instruments are housed in a cabinet with a strong sealing capacity, and the laser beams are sent out therefrom through the aperture plate.

However, in the case where the aperture plate is placed in an actual production line, liquid, powder and the like sometimes adhere to this aperture plate. In this case, the transmittance of the portion concerned is lowered. When the laser beam is incident onto the portion where the transmittance is lowered, the portion absorbs energy of the laser beam and is heated; and the concerned portion of the aperture plate is damaged. Then, when irradiation of the laser beam is continued, the damage advances and expands. When the damage as described above occurs, then in the conventional condensing system, such a damaged portion functions as, so to say, a light shielding mask, and the light quantity distribution in the shape of the condensed spot becomes nonuniform.

In contrast, in each of the property measurement systems 1 shown in FIG. 1 and FIG. 9, the light quantity distribution of the pulse laser beams can be made uniform in the condensed spot SP of the surface 101 of the metal material 100. That is to say, even if the beam profile of the pulse laser beam Lp that passes through the aperture plate 51 is deteriorated by the damaged portion of the aperture plate 51, to which the liquid, the powder and the like have adhered, the diffusion of the pulse ultrasonic wave SW to be excited in the metal material 100 is suppressed to be small. As a result, the amplitude of the pulse ultrasonic wave SW is less likely to be reduced with respect to the propagation distance, and the signal-to-noise ratio of the waveform of the ultrasonic wave, which is to be detected by the laser interferometer 41, is hardly changed. That is to say, even in the case where the aperture plate 51 is damaged, it is possible to maintain good measurement accuracy. Hence, even if the aperture plate 51 is damaged, it is not necessary to replace the aperture plate 51 instantaneously, and the aperture plate 51 just needs to be replaced in accordance with an idle period in the production schedule. Therefore, it is possible to avoid lowering the service frequency of the property measurement system 1.

Second Embodiment

Figure 10:
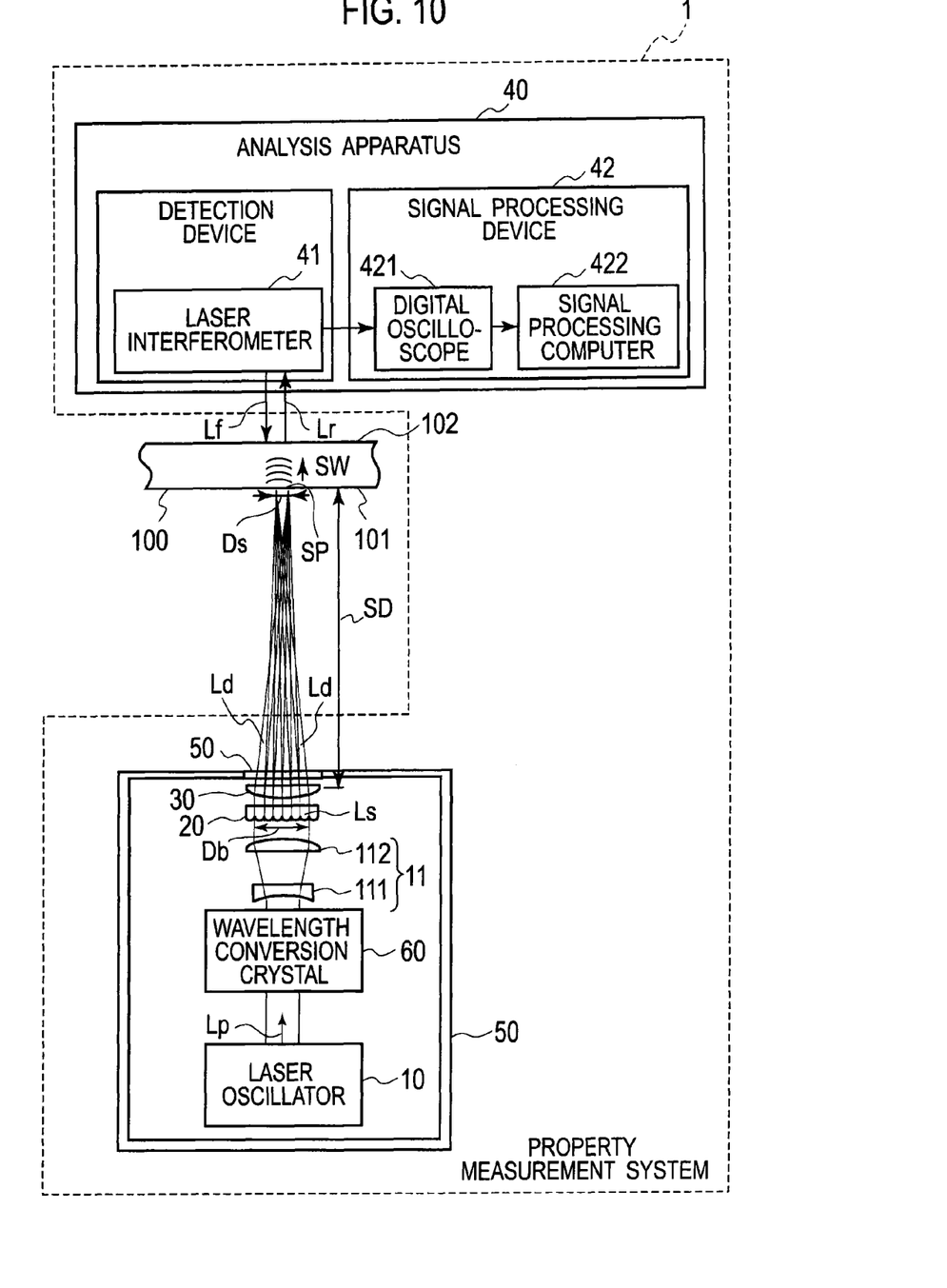
FIG. 10 is a schematic view showing a configuration of a property measurement system for a metal material according to a second embodiment of the present invention.

As shown in FIG. 10, a property measurement system 1 for a metal material according to a second embodiment of the present invention is different from the property measurement system 1 for a metal material according to the first embodiment, which is shown in FIG. 1, in further including a wavelength conversion crystal 60 that converts the wavelength of the pulse laser beam Lp emitted from the laser oscillator 10. Other configurations are similar to those of the first embodiment.

Absorptivity of the laser beam on the polished surface 101 of the metal material 100 becomes larger as the wavelength thereof becomes shorter. Hence, the pulse laser beam Lp to be emitted from the laser oscillator 10 is converted into a beam with a short wavelength by the wavelength conversion crystal 60, and is then irradiated onto the metal material 100, whereby, in such a high-reflectance metal material having the polished surface, a pulse ultrasonic wave SW with larger amplitude can be excited with respect to the same output of the pulse laser beam.

In accordance with the property measurement system 1 shown in FIG. 10, the pulse laser beam Lp to be emitted from the laser oscillator 10 is converted into a beam with a shorter wavelength by the wavelength conversion crystal 60, and is then irradiated onto the metal material 100. As the wavelength is shorter, the absorptivity of the laser beam by the surface 101 of the metal material 100 is larger, and accordingly, the pulse ultrasonic wave SW with a larger amplitude can be excited with respect to the same output of the pulse laser beam on the polished surface and the like. For example, the pulse laser beam Lp from the Nd:YAG laser with a wavelength of 1064 nm is converted into a pulse laser beam Lp with a wavelength of 532 nm or a wavelength of 355 nm by the wavelength conversion crystal 60 such as LBO($LiB_3O_5$) and KTP($KTiOPO_4$), and is then irradiated onto the surface 101 of the metal material 100.

Usually, in order to prevent damage of the wavelength conversion crystal 60, the light quantity density of the pulse laser beam Lp to be incident onto the wavelength conversion crystal 60 is set at a damage threshold value or less. Hence, if the output of the pulse laser beam Lp is large, then it is necessary to increase the beam diameter of the pulse laser beam Lp, which is to be incident, by using such a large-size wavelength conversion crystal 60.

Figure 11A:
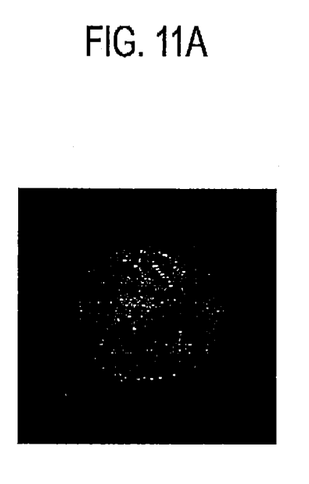
FIG. 11(a) is a photograph showing the beam profile before the chronological change.
Figure 11B:
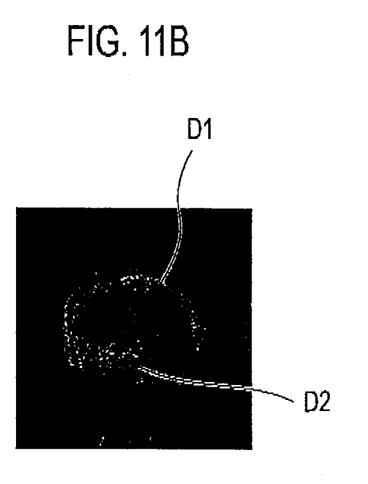
FIG. 11b is a photograph showing the beam profile after the chronological change.

However, if the large-size wavelength conversion crystal 60 is used, then there is a problem that the beam profile of the laser beam to be emitted from the wavelength conversion crystal 60 is deteriorated by temperature non-uniformity in the crystal and chronological change of the crystal concerned. For example, FIG. 11(a) and FIG. 11(b) show an example of chronological change of the beam profile in the case where the wavelength of the YAG laser beam is converted into 532 nm. FIG. 11(a) is a beam profile immediately after use of the wavelength conversion crystal 60 is started, and FIG. 11(b) is a beam profile after 10 months have elapsed from the start of the use.

In FIG. 11(b), a region D1 with a large light quantity and a region D2 with a small light quantity are mixedly present. As described above, when FIG. 11(a) and FIG. 11(b) are compared with each other, it is understood that the beam profile is largely changed chronologically. The deterioration of the beam profile, which is as described above, affects the diffusion status of the pulse ultrasonic wave SW, which is to be excited in the metal material 100, to an unignorable extent. That is to say, the amplitude of the ultrasonic wave is remarkably reduced with respect to the propagation distance, and the signal-to-noise ratio of the waveform of the ultrasonic wave to be detected by the laser interferometer 41 is deteriorated. As a result, there is a problem that the measurement accuracy is lowered.

In contrast to this, in accordance with the property measurement system 1 shown in FIG. 10, even if the deterioration of the beam profile occurs by chronological change, temperature non-uniformity and the like of the wavelength conversion crystal 60, the light quantity distribution of the pulse laser beam in the condensed spot SP of the surface 101 of the metal material 100 can be made uniform. Therefore, the diffusion of the pulse ultrasonic wave SW to be excited in the metal material 100 can be suppressed to be small. As a result, the amplitude of the pulse ultrasonic wave SW becomes less likely to be reduced with respect to the propagation distance, and the signal-to-noise ratio of the waveform of the ultrasonic wave, which is to be detected by the laser interferometer 41, is enhanced, whereby it is possible to obtain good measurement accuracy.

Other portions of the system are substantially similar to those of the first embodiment, and a duplicate description is omitted.

As above, the present invention has been described by the first and second embodiments; however, it should not be understood that the description and the drawings, which form a part of this disclosure, limit this invention. From this disclosure, varieties of alternative embodiments, examples and application technologies will be apparent for those skilled in the art. That is to say, it is a matter of course that the present invention incorporates a variety of embodiments and the like, which are not described herein. Hence, the technical scope of the present invention is determined only by the invention specifying items according to the scope of claims reasonable from the above description.

INDUSTRIAL APPLICABILITY

The property measurement system for a metal material according to the present invention is usable in manufacturing industries, which measure properties of metal materials in a non-contact manner.

REFERENCE SIGNS LIST

1 PROPERTY MEASUREMENT SYSTEM
10 LASER OSCILLATOR
11 MAGNIFICATION SYSTEM
20 LENS ARRAY
30 CONDENSING LENS
40 ANALYSIS APPARATUS
41 LASER INTERFEROMETER
42 SIGNAL PROCESSING DEVICE
50 CABINET
51 APERTURE PLATE
60 WAVELENGTH CONVERSION CRYSTAL
100 METAL MATERIAL
101 SURFACE
102 BACK SURFACE
111 CONCAVE LENS
112 CONVEX LENS
421 DIGITAL OSCILLOSCOPE
422 SIGNAL PROCESSING COMPUTER

The invention claimed is:

1. A property measurement system for a metal material, comprising:

a laser oscillator configured to emit a pulse laser beam;

a lens array that has a plurality of small lenses with a same shape, the small lenses being laid in a matrix on a plane perpendicular to an optical axis of the pulse laser beam, and arranged so that a part of a cross section of the pulse laser beam can be made incident onto each of the plurality of small lenses;

a condensing lens configured to overlap and condense emitted beams coming from the plurality of small lenses of the lens array on a same region of a surface of the metal material as a measurement target so that a light quantity density ensures ablation on a condensed spot;

an aperture plate placed between the metal material and the lens array and the condensing lens, the pulse laser beam that is condensed by the condensing lens passing through the aperture plate;

a laser interferometer configured to detect, as an electric signal, a pulse ultrasonic wave that is excited by the pulse laser beam condensed by the condensing lens and propagates through an inside of the metal material; and a signal processing computer configured to process the electric signal, wherein a spot size of the condensed spot is more than a predetermined threshold to suppress diffusion of the pulse ultrasonic wave.

2. The property measurement system of claim 1, further comprising:

a wavelength conversion crystal configured to convert a wavelength of the pulse laser beam emitted from the laser oscillator, the wavelength conversion crystal being provided between the laser oscillator and the lens array.

3. The property measurement system of claim 1, wherein the laser interferometer detects multiple reflection echoes of longitudinal wave components of the pulse ultrasonic wave.

4. The property measurement system of claim 1, wherein the ablation causes explosions that excite a pulse ultrasonic wave in the metal material.

* * * * *